United States Patent [19]

Zerbes et al.

[11] Patent Number: 5,639,886
[45] Date of Patent: Jun. 17, 1997

[54] ONE-POT PROCESS FOR THE PREPARATION OF 3-QUINOLONECARBOXYLIC ACID DERIVATIVES

[75] Inventors: Rudolf Zerbes; Paul Naab; Gerhard Franckowiak, all of Wuppertal; Herbert Diehl, Leverkusen, all of Germany

[73] Assignee: Bayer Aktiengesellschaft, Leverkusen, Germany

[21] Appl. No.: 348,400

[22] Filed: Dec. 2, 1994

[30] Foreign Application Priority Data

Dec. 10, 1993 [DE] Germany ............... 43 42 186.5

[51] Int. Cl.$^6$ ............... C07D 215/227; C07D 215/38
[52] U.S. Cl. ............... 546/155; 546/156; 546/157
[58] Field of Search ............... 546/155, 156, 546/157

[56] References Cited

U.S. PATENT DOCUMENTS

| | | | |
|---|---|---|---|
| 4,780,468 | 10/1988 | Bridges et al. | 514/312 |
| 4,894,458 | 1/1990 | Masuzawa et al. | 546/156 |
| 4,990,517 | 2/1991 | Petersen et al. | 514/300 |
| 5,037,834 | 8/1991 | Brighty et al. | 514/47 |
| 5,468,861 | 11/1995 | Petersen | 546/156 |
| 5,496,947 | 3/1996 | Yoon | 544/362 |
| 5,498,615 | 3/1996 | Kim | 514/300 |

FOREIGN PATENT DOCUMENTS

| | | |
|---|---|---|
| 0167763 | 1/1986 | European Pat. Off. . |
| 0275971 | 7/1988 | European Pat. Off. . |
| 0300311 | 1/1989 | European Pat. Off. . |
| 0350733 | 1/1990 | European Pat. Off. . |
| 550903 | 7/1993 | European Pat. Off. . |
| 4208789 | 9/1993 | Germany . |
| 4208792 | 9/1993 | Germany . |

OTHER PUBLICATIONS

Grohe, "Syntheses von 4–Chinolon–3–carbonsauren", Liebigs Ann Chem, vol. 1987, No. 1, pp. 29–37, 1987.

*Primary Examiner*—C. Warren Ivy
*Assistant Examiner*—D. Margaret M. Mach
*Attorney, Agent, or Firm*—Sprung Horn Kramer & Woods

[57] ABSTRACT

The present invention relates to a one-pot process for the preparation of 7-heterocyclyl-substituted 3-quinolonecarboxylic acid derivatives. They possess a strong anti-microbial effect. They include active compounds such as, for example, ofloxacin, ciprofloxacin or enrofloxacin.

11 Claims, No Drawings

ONE-POT PROCESS FOR THE PREPARATION OF 3-QUINOLONECARBOXYLIC ACID DERIVATIVES

The present invention relates to a one-pot process for the preparation of 7-heterocyclyl-substituted 3-quinolonecarboxlic acid derivatives. Compounds of this type are known per se. They possess a strong anti-microbial effect. They include active compounds such as, for example, ofloxacin, ciprofloxacin or enrofloxacin.

Compounds of this class which are to be prepared in accordance with the invention are substituted in the 7 position by heterocycles which, as the hetero atom, contain at least one nitrogen atom, but can, additionally, also contain oxygen, sulphur or additional nitrogen atoms. These heterocycles may also be substituted. Examples of monocyclic substituents which may be mentioned are piperazinyl, N-ethylpiperazinyl, pyrrolidinyl, 3-aminopyrrolidinyl, morpholinyl or thiomorpholinyl.

In one embodiment, the present invention relates to those 3-quinolonecarboxylic acid derivatives which are substituted in the 7 position by a bicyclic heterocycle, that is to say a one-pot process for the preparation of 3-quinolonecarboxylic acid derivatives of the general formula

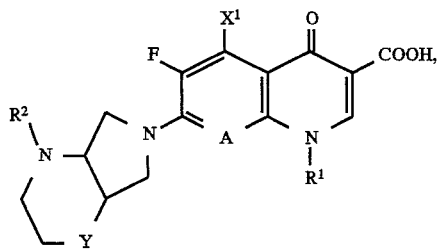

in which

A represents CH, CF, CCl, C—OCH$_3$ or C—CH$_3$,

X$^1$ represents H, halogen, NE$_2$ or CH$_3$,

Y represents CH$_2$ or O,

R$^1$ represents C$_1$–C$_3$-alkyl, FCH$_2$CH$_2$— or cyclopropyl, or phenyl or cyclopropyl which are optionally substituted once to three times by halogen, R$^2$ represents hydrogen, 5-methyl-2-oxo-1,3-dioxolen-4-yl-methyl C$_2$–C$_5$-oxoalkyl CH$_2$—CO—C$_6$H$_5$, CH$_2$CH$_2$CO$_2$R$^6$, R$^6$O$_2$C—CH=C—CO$_2$R$^6$, —CH=CH—CO$_2$R$^6$ or CH$_2$CH$_2$—CN, in which R$^6$ denotes hydrogen or C$_1$–C$_3$-alkyl.

Quinolonecarboxylic acid derivatives of this type are valuable pharmaceutical active compounds. They are suitable for use in the preparation of anti-microbial agents.

Various processes for the preparation of quinolonecarboxylic acid derivatives have been known hitherto.

According to EP-A-0 167 763, compounds of the formula (II) (Z$^1$, Z$^2$ and Z$^3$ are, independently of each other, fluorine or chlorine)

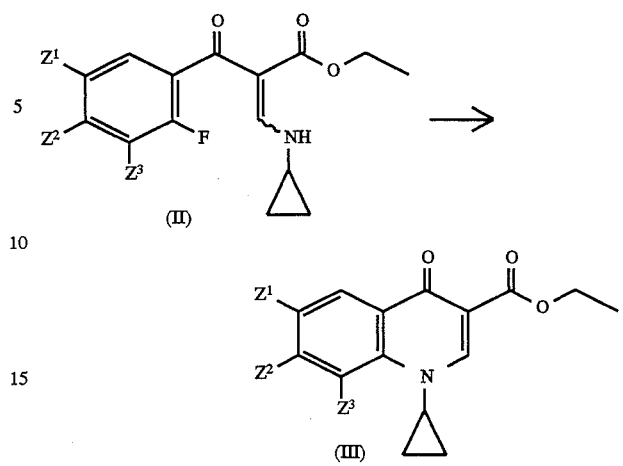

are cyclized at temperatures of from 60° C. to 300° C. in the presence of a base such as alkali metal fluoride or alkali metal carbonate in a solvent such as DMF, HMPT or NMP. The ester (III) is hydrolysed in a following step to the acid (IV). The latter is subsequently reacted with optionally cyclic amines (V), preferably in solvents, to form the substituted derivatives (VI).

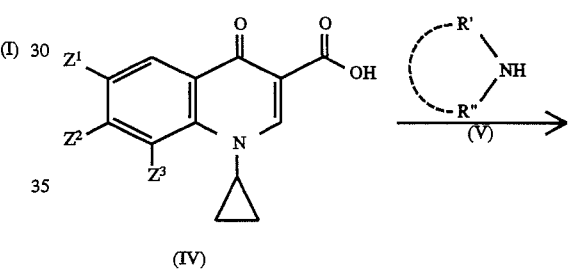

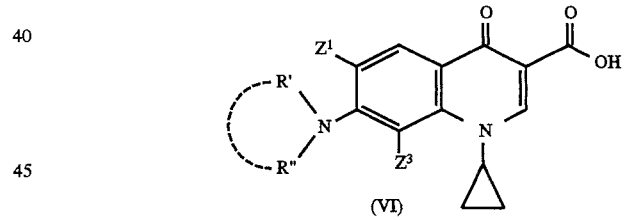

However, the total yield from (II) to (VI) is, at 56%, unsatisfactory. Moreover, in association with the alkaline hydrolysis of the ester (III), by-products can arise in which Z$^2$ was substituted by hydroxyl or alkoxy, as can oligomers and polymers, in particular when Z$^2$ represents fluorine. If the hydrolysis is carried out under acidic conditions, hydrogen fluoride is liberated, leading to corrosion of the production plant and to contamination of the product with complex metal fluorides. This is particularly the case when, after the cyclization of (II) to (III), in which HF arises and is bound to a base, this reaction mixture is employed, without prior isolation of the ester (III), for the acid hydrolysis, during which, inevitably, the hydrogen fluoride which was previously bound to base is liberated once more.

According to EP-A-0 275 971, compounds of the formula (XI) can be obtained by introducing the amine (V') prior to the ring closure:

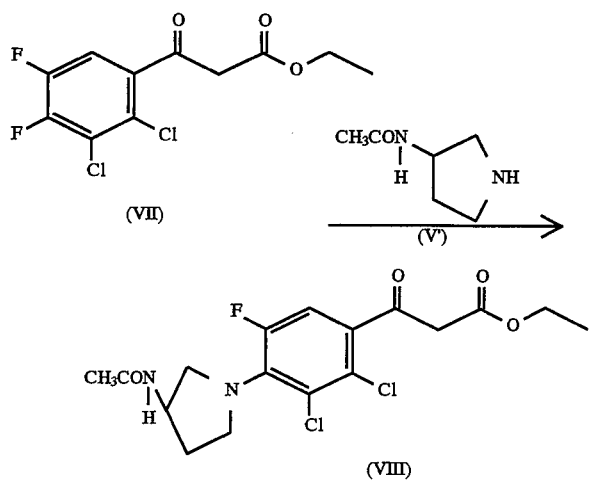

(VII)  (V')

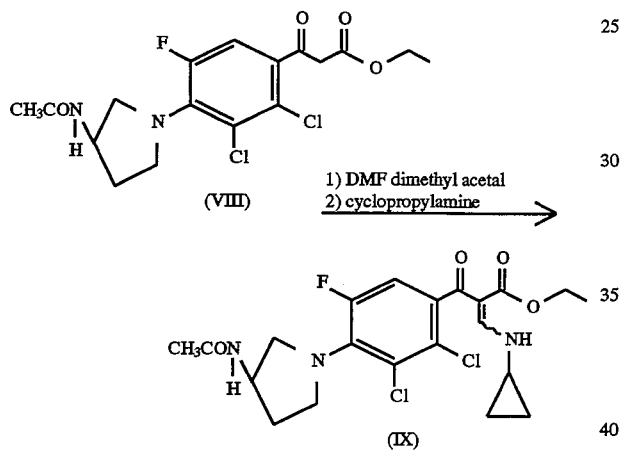

(VIII)

The cyclopropylaminoacrylate precursor (IX) corresponding to the above compound (II) is then synthesized:

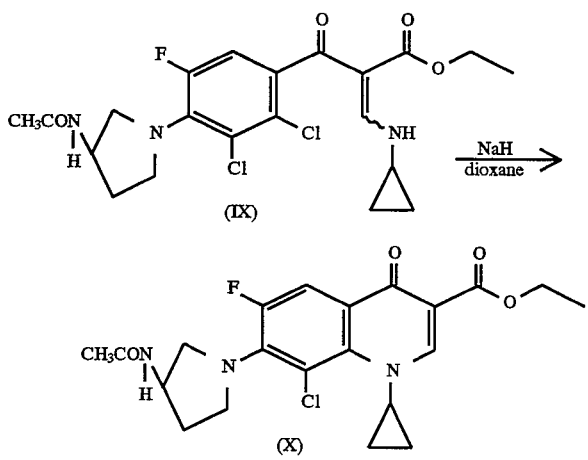

(VIII)

1) DMF dimethyl acetal
2) cyclopropylamine (IX)

The cyclization of (IX) in the presence of strong bases, such as, for example NaH, gives rise to the ester (X):

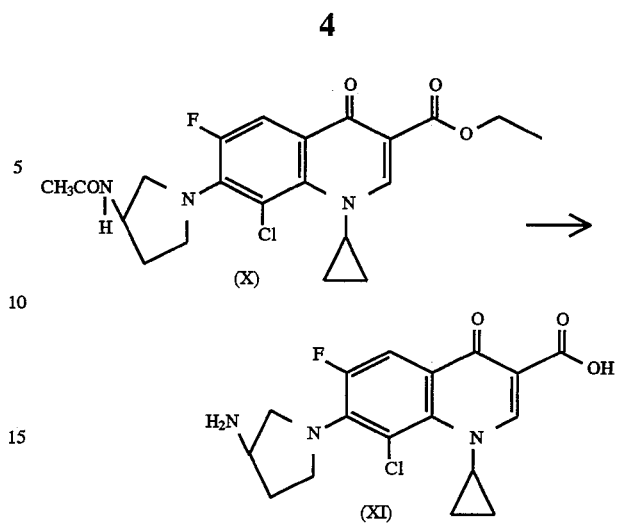

(IX)

NaH / dioxane (X)

Finally, the target compound (XI) is obtained by hydrolysing (X):

(X)

(XI)

However, the total yield from (VII) to (XI) is only 15%, so that a process of this type is very uneconomical.

EP-A-0 350 733 also discloses a multi-step process according to which quinolonecarboxylic acids with an antibacterial action are obtained by reacting the carboxylic acids (XII, R³=H) with a mines, some of which are bicyclic.

However, the yield, proceeding from the aminoacrylate precursor, is, at approximately 60%, not satisfactory. Moreover, in this case as well, there exists the problem of the undesirable substitution of the 7 halogen by hydroxyl or alkoxy, especially in association with the alkaline hydrolysis of the ester (XII, R³=alkyl).

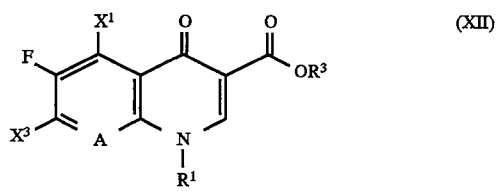

A, X¹, R¹ cf. (I)
X³=halogen, preferably fluorine

These disadvantages—multi-step synthesis, low yields, foundation of corrosive cleavage products, and contamination of the end products—render the large-scale production of these active compounds more difficult.

In order to avoid multi-step synthesis processes, consideration can be given to the development of so-called one-pot processes. In these processes, the synthesis is carried out in one and the same reaction vessel, without isolating the intermediates, by consecutive addition of the reactants. EP-A-0 300 311 discloses such a process for synthesizing type (IV) precursors of (VI) quinolonecarboxylic acid derivatives.

However, the process described in that publication ends at the step of a quinolonecarboxylic acid (analogous to IV), which would subsequently have to be reacted with the amine to be introduced in the 7 position. Accordingly, the above-described disadvantages cannot be avoided.

An advantageous one-pot process for the preparation of 7-heterocyclyl-substituted quinolonecarboxylic acid derivatives has now been found, in which process it is not only the above-described disadvantages with regard to the formation of undesirable 7-hydroxy by-products and the plant corrosion due to liberated hydrogen fluoride which are dispensed with in their entirety. In addition to this, the desired active compounds (I) are made available, at high purity, in yields which are usually greater than 90%, based on the step (XIII) or the step (XXVI).

According to the invention, an acid halide of the formula (XXVI)

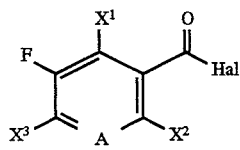

(XXVI)

in which

Hal, $X^2$ and $X^3$ represent fluorine or chlorine, and A and $X^1$ have the meanings given for formula (I), is either reacted in a solvent with a dimethylaminoacrylic acid ester of the formula $(CH_3)_2N-CH=CH-COOR$, after which the aminoacrylic ester (XIII) is produced by adding an amine $R^1\text{-}NH_2$, with amine exchange in the acrylic ester moiety of the primary product, or the acid halide (XXVI) is immediately reacted with an aminoacrylic ester of the formula $R^1NH-CH=CH-COOR$, in which case the above-described amine exchange is dispensed with and the compound (XIII) is produced directly.

This aminoacrylic ester of the formula (XIII), in which A, $X^1$ and $R^1$ have the meanings given for formula (I), $X^2$ and $X^3$ represent halogen, and R represents a customary organic radical which is suitable for ester formation, preferably methyl, ethyl or propyl, is heated in the same solvent with an auxiliary base, and thereby cyclized to form the ester (XIV).

The heterocycle, for example the amine (XVII), is then added to this mixture and, after formation of the 7-substitution product (XVI) is complete, the 3-ester function is hydrolysed by adding a strong base. The reaction mixture is finally rendered neutral by adding an acid and the product (I), which precipitates, is isolated. The following formula scheme illustrates, by way of example, the sequence of reactions in this one-pot process:

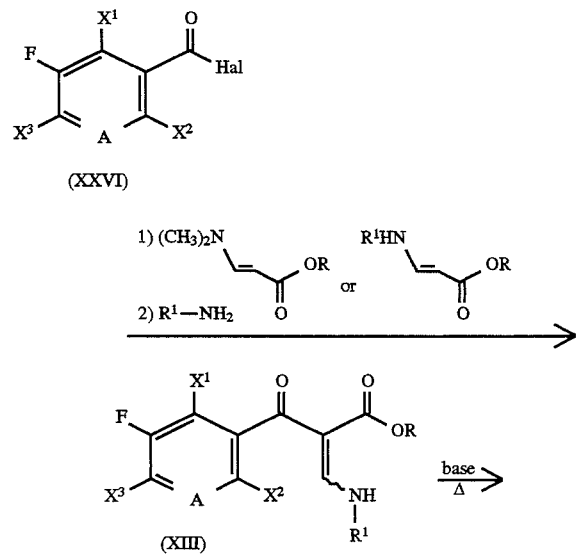

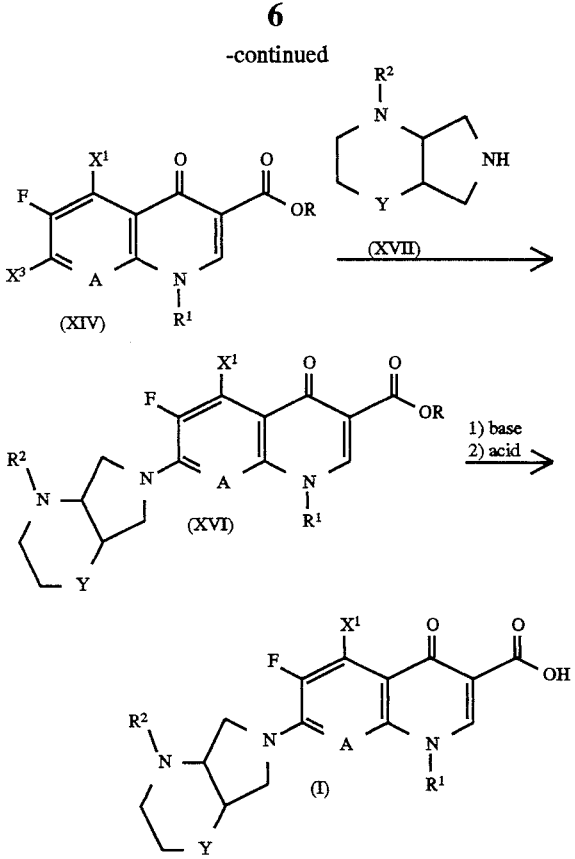

In the formulae(I) as well as (XIII), (XIV), (XVI) and (XVII), the symbols generally have the following meanings:

A represents CH, CF, CCl, C—$OCH_3$ or C—$CH_3$,

R represents a customary organic radical which is suitable for ester formation, preferably ethyl, methyl or propyl, $R^1$ represents $C_1$-$C_3$-alkyl, $FCH_2CH_2$- or cyclopropyl, or phenyl or cyclopropyl which are optionally substituted once to three times by halogen, $R^2$ represents hydrogen, 5-methyl-2-oxo-1,3-dioxolen-4-yl-methyl $C_2$-$C_5$-oxoalkyl, $CH_2$—CO—$C_6H_5$ $CH_2CH_2CO$ $R^6$, $R^6O_2C$—C=C—$CO_2R^6$, —CH=CH—$CO_2R^6$, or $CH_2CH_2$—CN, in which $R^6$ denotes hydrogen or $C_1$-$C_3$-alkyl, Y represents $CH_2$ or O, $X^1$ represents H, halogen, $NH_2$ or $CH_3$, and $X^2$ and $X^3$ represent halogen.

According to the invention, the synthesis of compounds (I) is preferably carried out using precursors (XIII) and (XVII) in which A represents CH, CF, CCl, C—$OCH_3$ or C—$CH_3$, R represents $C_1$-$C_4$-alkyl, $C_6H_5$ or $Si(CH_3)_3$, $R^1$ represents $C_2H_5$, cyclopropyl which is optionally substituted once to three times by fluorine, or 2,4-difluorophenyl, $R^2$ represents H, $CH_2$—O—$CH_3$, $CH_2$—O—$C_6H_5$, $CH_2CH_2$—CO—$CH_3$, $CH_2CH_2CO_2R^6$, $R^6O_2C$—CH=C—$CO_2R^6$, —CH=$CO_2R^6$ or $CH_2CH_2CN$, in which $R^6$ denotes $C_1$-$C_3$-alkyl, Y represents $CH_2$ or O, $X^1$ represents hydrogen or halogen, and $X^2$ and $X^3$ represent chlorine or fluorine.

Compounds of the abovementioned formulae are particularly preferred in which

A represents CCl or CF,
R represents CH₃ or C₂H₅,
R¹ represents cyclopropyl,
R² represents hydrogen,
Y represents CH₂,
X¹ represents hydrogen,
X² represents fluorine or chlorine, and
X³ represents fluorine.

3-Quinolonecarboxylic acid derivatives of the general formula (Ib),

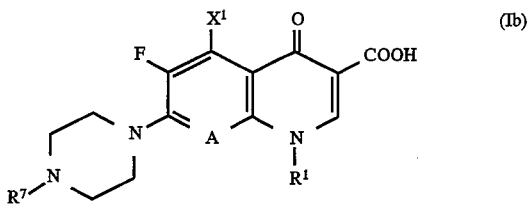
(Ib)

in which

A represents CH, CF, CCl, C—OCH₃ or C—CH₃,

X¹ represents H, halogen, NH₂ or CH₃,

R¹ represents $C_1$–$C_3$-alkyl, FCH₂CH₂- or cyclopropyl, or phenyl or cyclopropyl which are optionally substituted once to three times by halogen, and R⁷ represents hydrogen, optionally substituted alkyl or phenyl, or a customary group which is suitable for protecting a nitrogen atom, preferably, however, ethyl, are also prepared in accordance with the invention by reacting, without isolation of the intermediates, an acid halide of the formula (XXVI)

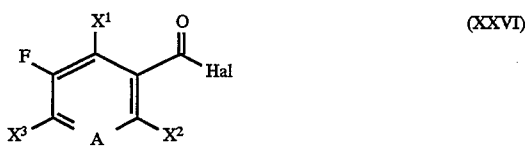
(XXVI)

in which

Hal, X² and X³ represent fluorine or chlorine and A and X¹ have the abovementioned meanings, in a solvent with a dimethylaminoacrylic acid ester of the formula

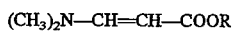

(CH₃)₂N—CH=CH—COOR after which the aminoacrylic ester (XIII),

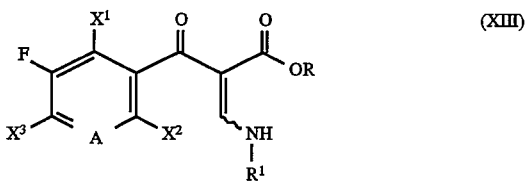
(XIII)

in which A, X¹ and R¹ have the meanings given for the formula (Ib), X² and X³ represent halogen, and R represents a customary organic radical which is suitable for ester formation, preferably methyl, ethyl or propyl; is produced by adding an amine R¹-NH₂, with amine exchange in the acrylic ester moiety of the primary product, and is then heated in a solvent with an auxiliary base, and thereby cyclized to form compounds of the general formula (XIV),

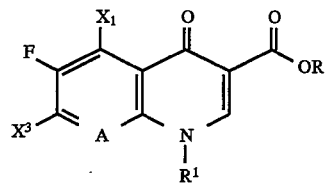
(XIV)

in which A, R, R¹, X¹ and X³ have the abovementioned meanings, which are converted, by reaction with compounds of the general formula (XV)

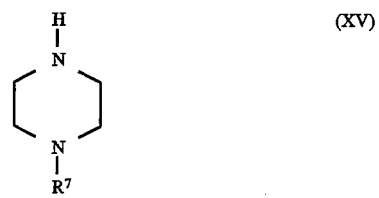
(XV)

in which

R⁷ has the abovementioned meaning, into esters of the general formula (XXVII)

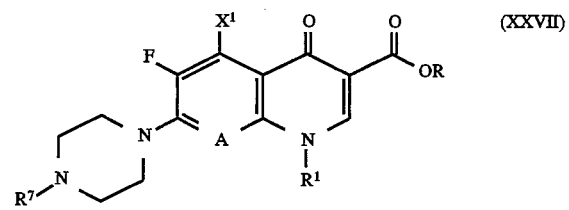
(XXVII)

in which A, R, R¹, R⁷ and X¹ have the abovementioned meanings, from which the 3-quinolonecarboxylic acid derivatives of the formula (Ib) result, by means of alkaline hydrolysis of the ester function, and are precipitated by neutralizing the reaction mixture.

The compounds (I) which are particularly preferably to be prepared by the process according to the invention also include optically active derivatives, obtainable by reacting (XIII) with enantiomerically pure amines (XVII a–d), which are described in DE-A-4 208 789 and DE-A-4 208 792.

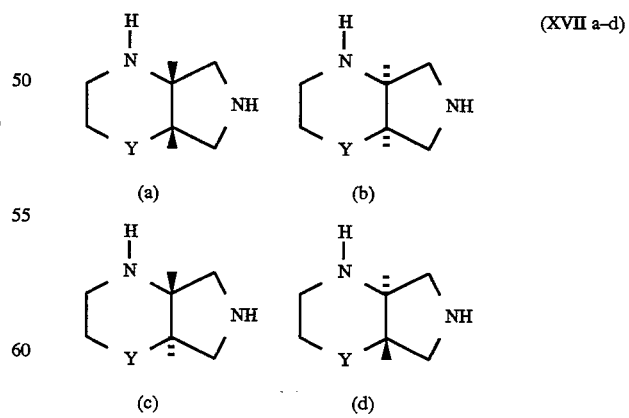
(XVII a–d)

(a)   (b)

(c)   (d)

Examples of individual compounds which may particularly preferably be prepared in accordance with the invention are

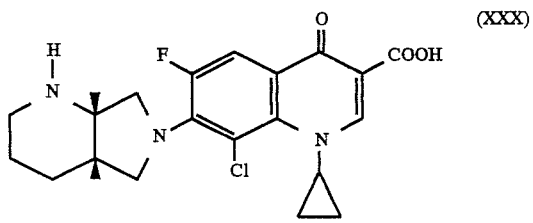

8-chloro-1-cyclopropyl-7-([S, S]-2,8-diazabicyclo[4.3.0.]-non-8-yl)-6-fluoro-1,4-dihydro-4-oxo-3-quinoline-carboxylic acid (XXX) and

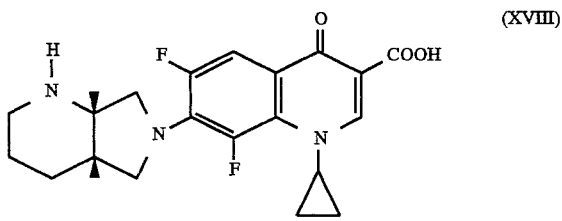

1-cyclopropyl-7-([S,S]-2,8-diazabicyclo[4.3.0.]non-8-yl)-6,8-difluoro-1,4-dihydro-4-oxo-3-quinolinecarboxylic acid (XVIII).

In principle, all common inert organic solvents may be used for carrying out the one-pot process according to the invention. Examples which may be mentioned are dimethylethyleneurea (DMEU), dimethylpropyleneurea (DMPU), N-methylcaprolactam, tert.-butanol, tetramethylurea, sulpholane and dimethoxyethane. Water-miscible solvents, such as N-methylpyrrolidone (NMP), diglyme, N,N-dimethylformamide (DMF) or dioxane, are preferably used, particularly preferably NMP.

The cyclization is carried out at the lowest temperature possible. Temperatures of from 60° C. to 100° C. are generally sufficient, something which can be ascertained, with the aid of exploratory preliminary experiments using the selected precursor (XIII) in the selected medium, solvent/auxiliary base, just as easily as can the optimal quantity of solvent.

Acid binders which are customary in organic synthesis may be used as auxiliary bases in the cyclization. Potassium tert.-butoxide, butyl-lithium, phenyl-lithium, sodium methoxide, sodium hydride, sodium carbonate, potassium carbonate, potassium fluoride and sodium fluoride may be mentioned, by way of example, for this reaction step. It can be advantageous to employ an excess of up to 10 mol % of base, where appropriate an even greater excess.

Sodium carbonate or potassium carbonate are preferably employed.

After cyclization is complete, the amine (XV) or (XVII), for example, is metered in at the same temperature, or, where appropriate, at a temperature which has been further increased. The optimum reaction temperature depends on the reactants but can, in turn, be ascertained without difficulty in a preliminary experiment. In general, temperatures of from 60° C. to 100° C. are adequate.

Once substitution of the 7 position in (XIV) is concluded, the reaction mixture is diluted and cooled by adding water. A volume of water corresponding approximately to that of the reaction mixture will generally be used. Alkali metal hydroxide solution, preferably sodium hydroxide solution, in equimolar quantity or up to an excess of about 10 mol %, is then added to hydrolyse the ester function. The hydrolysis is preferably carried out at approximately 60° C.

The reaction mixture is then further diluted with water, a volume of water as a rule being added which is approximately double that of the mixture. The mixture is adjusted to a pH of about 7.8 with mineral acid, preferably hydrochloric acid, or acetic acid, and is then, where appropriate, further cooled down to from 0° to 5° C.

The target product, for example (I) or (Ib), which precipitates at this stage is subsequently isolated, for example by filtration with suction.

As a rule, the product, for example (I) or (Ib), is obtained at a purity of >95% and in a yield of >85%, usually, however, of >90%, based on the starting compound (XIII).

The following implementation examples illustrate the invention:

1. Synthesis of 8-chloro-1-cyclopropyl-7-([S,S]-2,8-diazabicyclo[4.3.0]non-8-yl)-6-fluoro-1,4-dihydro-4-oxo-3-quinolinecarboxylic acid (XXX):

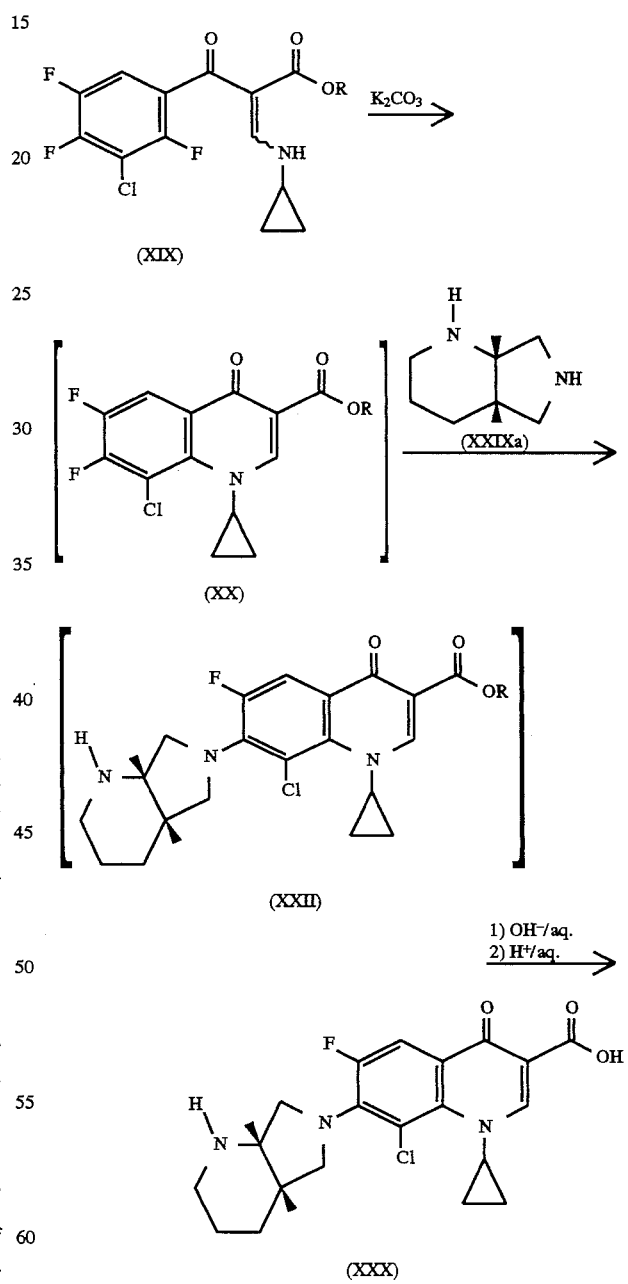

a) Via methyl ester (R=CH₃)

10.2 g of K₂CO₃ and 17.7 g (0.053 mol) of XIX (methyl ester) are heated at 60° C. for 50 min in 30 ml of NMP.

7.5 g (0.059 mol) of S,S-pyrrolopiperidine (XXIXa) are added and the mixture is stirred at 90° C. for 90 min.

The resulting ester (XXII) is hydrolysed at 60° C. in 50 min using 33 g of 8.5% sodium hydroxide solution. The mixture is diluted with 120 ml of water and then adjusted to a pH of 7.8 using 6N hydrochloric acid.

Once the mixture has been cooled down to 5° C. the precipitated product (XXX) is separated off on a Buchner funnel, then washed 3× with 100 ml of water on each occasion, and dried at 80° C. overnight in vacuo.

Yield: 19 g ≙ 86.1% of theory (at 97.5% by weight)

b) Via ethyl ester (R=C$_2$H$_5$)

20.4 g of K$_2$CO$_3$ and 36.8 g (0.106 mol) of (XIX) are heated at 80° C. for 2.5 hours in 60 ml of diglyme.

After adding 15 g (0.118 mol) of S,S-pyrrolopiperidine (XXIXa), the mixture is stirred at from 90° to 100° C. for 4 hours.

The resulting ester (XXII) is hydrolysed at 80° C. within 2.5 hours after adding 60 ml of water and 22 g of 45% sodium hydroxide solution. The mixture is diluted with 240 ml of water and adjusted to a pH of 7.8 with 6N hydrochloric acid.

Once the mixture has been cooled down to 5° C., the product (XXX) is filtered off with suction, washed with water, and dried at 70° C. in vacuo.

Yield: 43 g ≙ 96.5% of theory (at 96.5% by weight)

2) Synthesis of 1-cyclopropyl-7-([S,S]-2,8-diazabicyclo[4.3.0]non-8-yl)-6,8-difluoro-1,4-dihydro-4-oxo-3-quinolinecarboxylic acid (XVIII).

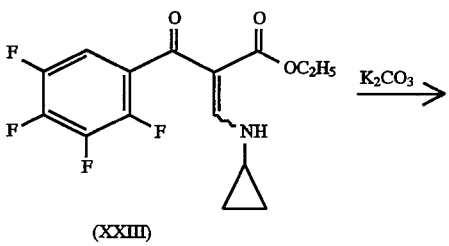

(XXIII)

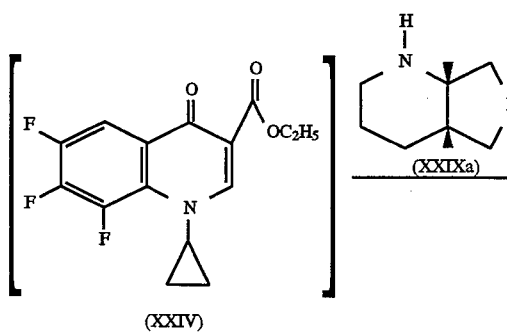

(XXIV)

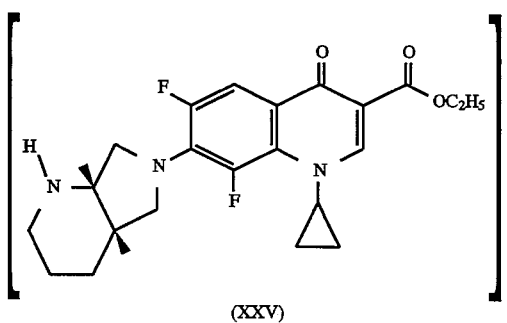

(XXV)

1) OH⁻/aq.
2) H⁺/aq.

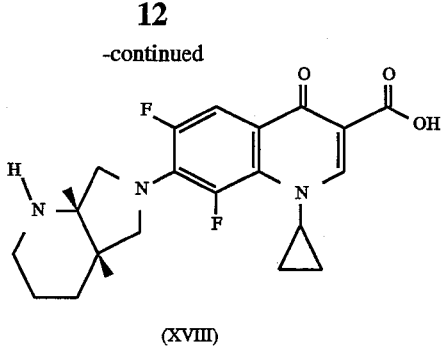

(XVIII)

20.4 g of K$_2$CO$_3$ and 35.2 g (0.106 mol) of (XXIII) are heated at 60° C. for 1 hour in 60 ml of NMP. (By HPLC, 97.6% of (XXIV) has resulted after 40 min).

15.5 g (0.12 mol) of S,S-pyrrolopiperidine (XXIXa) are added. 0.2% of (XXIV) is still present (HPLC) after 2 hours at 80° C.

Following the addition of 60 ml of water and NaOH, the resulting ester (XXV) is hydrolysed to (XVIII) in 4 hours at 60° C.

The mixture is diluted with 240 ml of water and adjusted to a pH of 7.8 with 6N hydrochloric acid.

The product is filtered off with suction, washed with water and dried at 70° C. in vacuo.

Yield: 38.1 g ≙ 91.4% Of theory (at 98.9% by weight)

3) Synthesis of 1-cyclopropyl-6-fluoro-7-(1-piperazinyl)-1,4-dihydro-4-oxo-3-quinolinecarboxylic acid (XXXIVa) and 1-cyclopropyl-6-fluoro-7-(4-ethyl-1-piperazinyl)-1,4-dihydro-4-oxo-3-quinolinecarboxylic acid (XXXIVa, b)

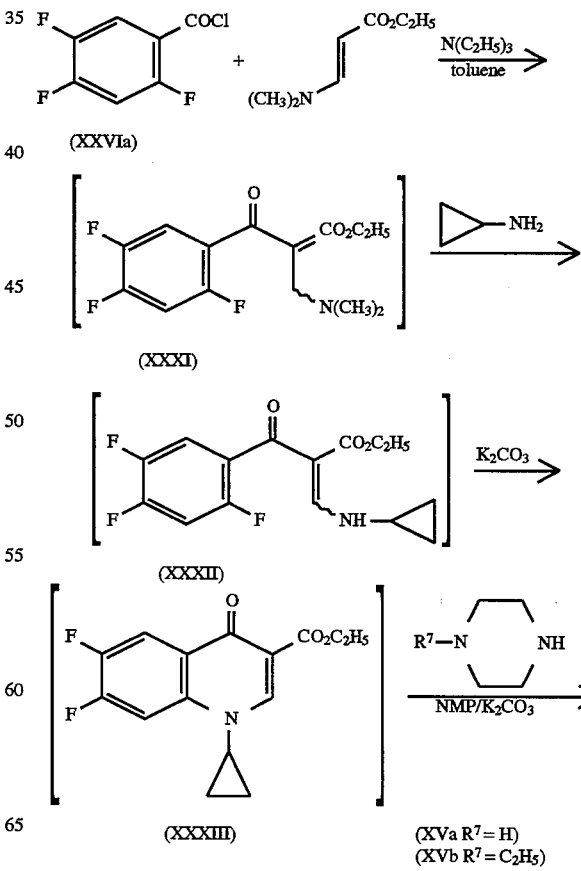

(XVa R$^7$ = H)
(XVb R$^7$ = C$_2$H$_5$)

-continued

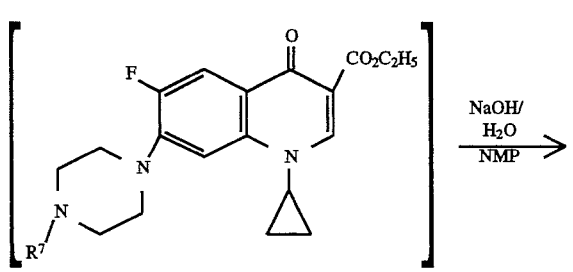

(XXVIIa R⁷ = H)
(XXVIIb R⁷ = C₂H₅)

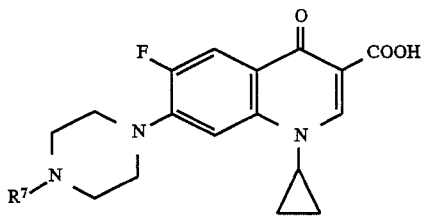

(XXXIVa R⁷ = H)
(XXXIVb R⁷ = C₂H₅)

35.8 g (0.25 mol) of ethyl dimethylaminoacrylate and 27.3 g (0.27 mol) of triethylamine are initially introduced in 50 ml of toluene, and 48.6 g (0.25 mol) of 2,4,5-trifluorobenzoyl chloride (XXVIa) are added dropwise at 50° C. within 30 minutes. The mixture is subsequently stirred at from 50 to 55° C. for 1 hour and 17.3 g (0.28 mol) of glacial acetic acid and 15.5 g (0.27 mol) of cyclopropylamine are then added dropwise at from 30 to 36° C. After 1 hour, the salts are extracted with 100 ml of water. The organic phase is concentrated by evaporation in water pump vacuum at 40° C. 80.3 g of (XXXII) are obtained as an oily residue.

The oil (XXXII) is dissolved by adding 250 ml of N-methylpyrrolidone and heated to from 80° to 90° C. together with 48.4 g (0.35 mol) of potassium carbonate. After 1 hour, 86 g (1 mol) of piperazine (XVa) or 114 g (1 mol) of N-ethylpiperazine (XVb), respectively, are added. The mixture is stirred at from 80° to 90° C. for one hour and then diluted with 150 ml of water.

After adding 20 g (0.5 mol) of NaOH, the temperature is maintained at 70° C. for 1 hour and the mixture is then further diluted with 500 ml of water. Small quantities of impurities in the solution are filtered off and the pH is adjusted to 7.5 with half-concentrated hydrochloric acid.

Once the mixture has been cooled down to from 0° to 5° C., the betain (XXXIV) is filtered off with suction after 2 hours and washed 2× with 200 ml of water on each occasion; the product is dried overnight in vacuo.

Yields: XXXIVa 71.4 g (98.0% by weight, HPLC) ≙ 84.5% of theory

XXXIVb 78.2 g (98.5% by weight, HPLC) ≙ 87.0% of theory

4) Synthesis of 1-cyclopropyl-6-fluoro-7-(1-piperazinyl)-1,4-dihydro-4-oxo-3-quinolinecarboxylic acid (XXXIVa) and 1-cyclopropyl-6-fluoro-7-(4-ethyl-1-piperazinyl)-1,4-dihydro-4-oxo-3-quinolinecarboxylic acid (XXXIVb)

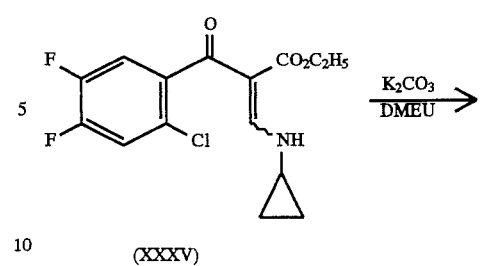

(XXXV)

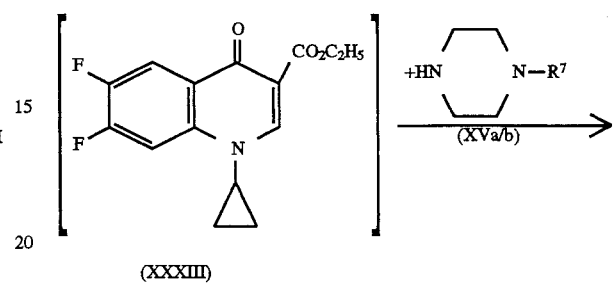

(XXXIII)

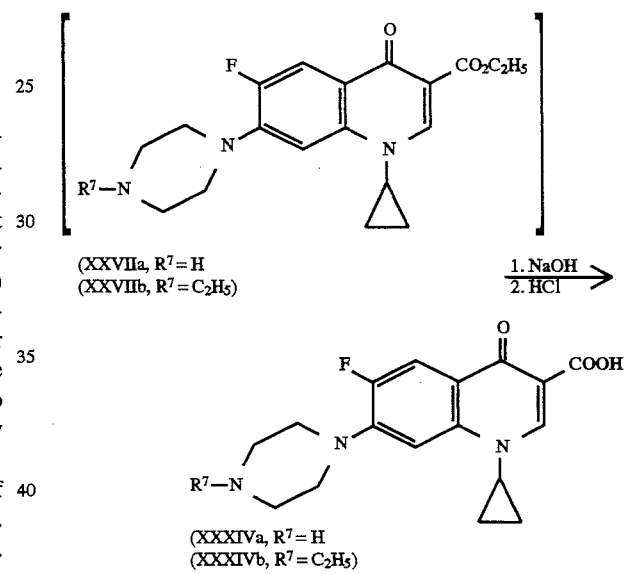

(XXVIIa, R⁷ = H)
(XXVIIb, R⁷ = C₂H₅)

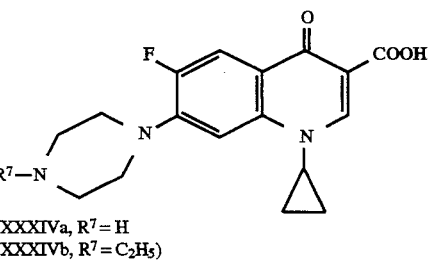

(XXXIVa, R⁷ = H)
(XXXIVb, R⁷ = C₂H₅)

82.4 g of (XXXv) are dissolved in 250 ml of DMEU and heated to from 100° to 120° C. together with 48.4 (0.35 mol) of potassium carbonate.

After 2 hours, 86 g (1 mol) of piperazine (XVa) or 114 g (1 mol) of N-ethylpiperazine (XVb), respectively, are added. The mixture is stirred at from 80° to 90° C. for one hour and then diluted with 150 ml of water.

After adding 20 g (0.5 mol) of NaOH, the temperature is maintained at 70° C. for 1 hour and the mixture is then diluted further with 500 ml of water. Small quantities of impurities in the solution are filtered off and the pH is adjusted to 7.5 with half-concentrated hydrochloric acid.

Once the mixture has been cooled down to from 0° to 5° C., the betain (XXXIV) is filtered off with suction after 2 hours and washed 2× with 200 ml of water on each occasion; the product is dried overnight in vacuo.

Yield: (XXXIVa): 73.0 g (98.5% by weight) ≙ 86.8% of A theory (XXXIVb): 77.2 g (99.0% by weight) ≙ 85.1% of theory 5) 7-(3-Amino-1-pyrrolidinyl)-8-chloro-1-cyclopropyl-6-fluoro-1,4-dihydro-4-oxo-3-quinolinecarboxylic acid (XI)

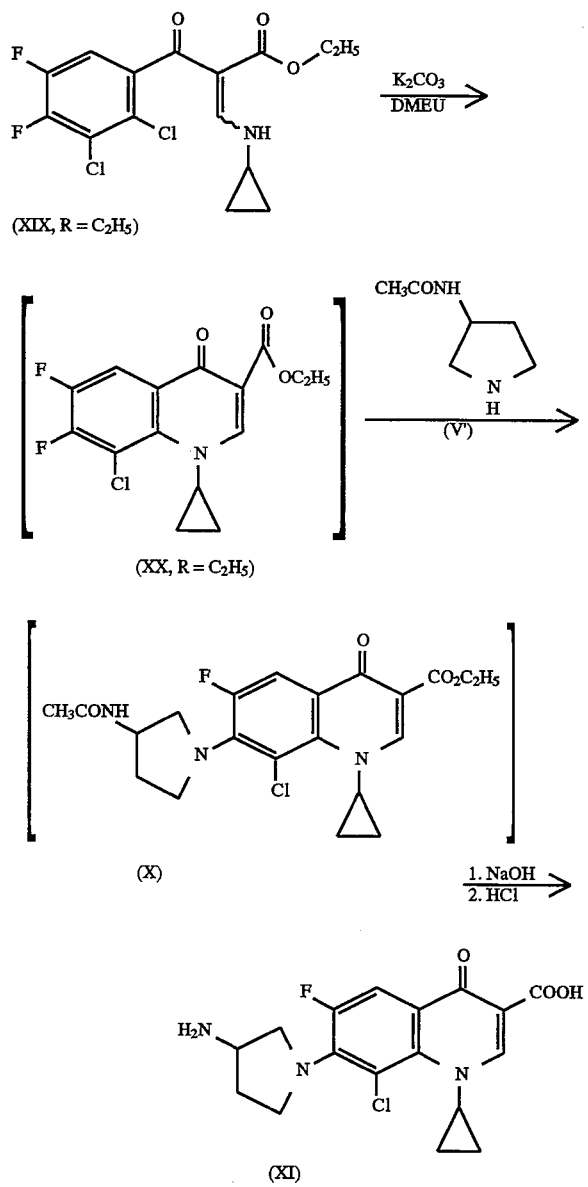

20.6 g of (XIX, R=C₂H₅) are dissolved in 65 ml of DMEU and heated at from 100 to 120° C. for 2 hours together with 12.2 g of K₂CO₃.

8.5 g of 3-acetamidopyrrolidine (V') are added, and the reaction mixture is subsequently stirred at from 80° C. to 90° C. for 1 hour. It is then diluted with 40 ml of water, and 10 g of NaOH are added. After 4 hours at from 90° to 100° C. the mixture is diluted with a further 125 ml of water, filtered and neutralized with half-concentrated hydrochloric acid.

The solid is filtered off, washed with water and isopropanol, and dried overnight in vacuo.

Yield: 17.3 g of (XI) (98.7% by weight, HPLC) ≙ 83% of theory.

EXAMPLE

Synthesis of 1-cyclopropyl-6-fluoro-7-(1-piperazinyl)-1,4-dihydro-4-oxo-3-quinolinecarboxylic acid (XXXIVa)

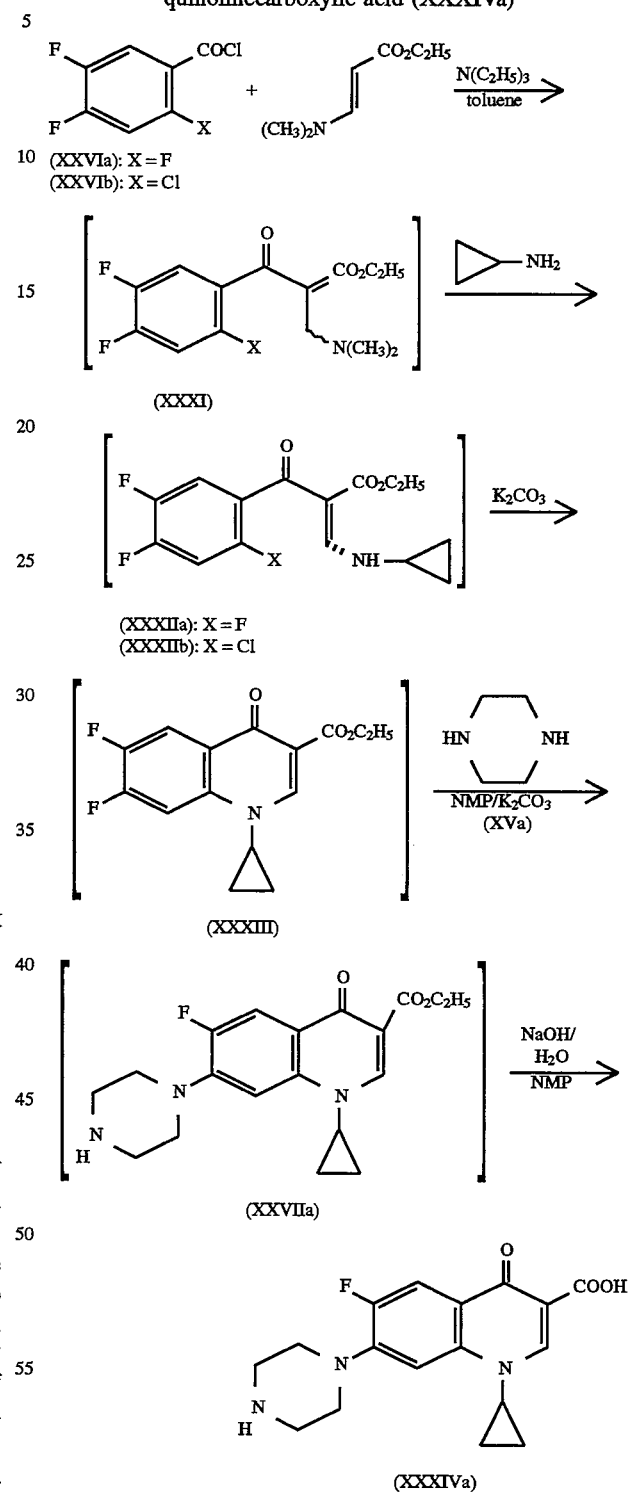

35.8 g (0.25 mol) of ethyl dimethylaminoacrylate and 27.3 g (0.27 mol) of triethylamine are initially introduced in 50 ml of toluene, and a mixture of 24.3 g (0.125 mol) of 2,4,5-trifluorobenzoyl chloride (XXVIa) and 26.3 g (0.125 mol) of 2-chloro-4,5-difluorobenzoyl chloride (XXVIb) are added dropwise at 50° C. within 30 minutes. The mixture is subsequently stirred at from 50° to 55° C. for 1 hour and 17.3 g (0.28 mol) of glacial acetic acid and 15.5 g (0.27 mol) of cyclopropylamine are then added dropwise at from 30° to 36° C. After 1 hour, the salts are extracted with 100 ml of water. The organic phase is concentrated by evaporation in water pump vacuum at 40° C. 81.5 g of (XXXIIa/b) are obtained as an oily residue.

The oil (XXXIIa/b) is dissolved by adding 250 ml of N-methylpyrrolidone and heated to from 90° C. to 120° C. together with 48.4 g (0.35 mol) of potassium carbonate. After 2 hours, 86 g (1 mol) of piperazine (XVa) are added. The mixture is stirred at from 80° to 90° C. for one hour and then diluted with 150 ml of water.

After adding 20 g (0.5 mol) of NaOH, the temperature is maintained at 70° C. for 1 hour and the mixture is then further diluted with 500 ml of water. Small quantities of impurities in the solution are filtered off and the pH is adjusted to 7.5 with half-concentrated hydrochloric acid.

Once the mixture has been cooled down to from 0° to 5° C., the betain (XXXIV) is filtered off with suction after 2 hours and washed 2× with 200 ml of water on each occasion; the product is dried overnight in vacuo.

Yields: XXXIVa 73,4 g (98.0% by weight, HPLC) $\hat{=}$ 86.5% of A theory.

We claim:
1. A one-pot process for the preparation of a 3-quinolone-carboxylic acid derivative of the formula

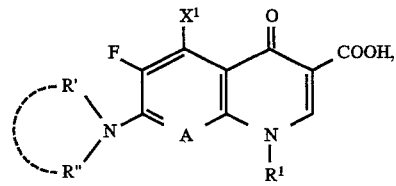

in which
R' and R", together with the nitrogen atom to which they are bonded, form an optionally substituted monocyclic or bicyclic heterocycle which can optionally contain at least one further nitrogen, oxygen or sulphur hetero atom in any ring part, A is CH, CF, CCl, C—OCH$_3$ or C—CH$_3$, X$^1$ is H, halogen, NH$_2$ or CH$_3$, R$^1$ is C$_1$–C$_3$-alkyl or FCH$_2$CH$_2$, or cyclopropyl or phenyl each of which is optionally substituted up to three times by halogen, which, without isolation of the intermediates after each step, comprises A) in a solvent selected from the group consisting of NMP, diglyme, DMEU, tetramethylurea and sulfolane, reacting an acid halide of the formula

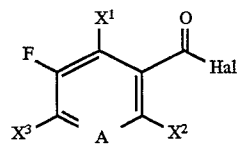

in which
Hal, X$^2$ and X$^3$ each independently is fluorine or chlorine, with i) a dimethylaminoacrylic acid ester of the formula

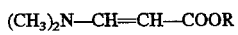

in which
R is methyl, ethyl or propyl, and then adding an amine of the formula

to form a solution of an aminoacrylic ester of the formula

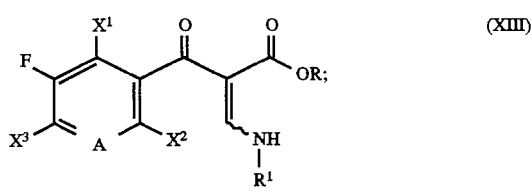

or with
ii) an aminoacrylic ester of the formula

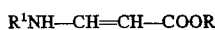

to form a solution of an aminoacrylic ester of the formula

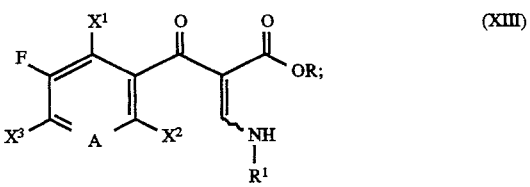

B) heating the solution of the compound (XIII) with an auxiliary base to effect cyclization and thereby to form a solution of a compound of the formula

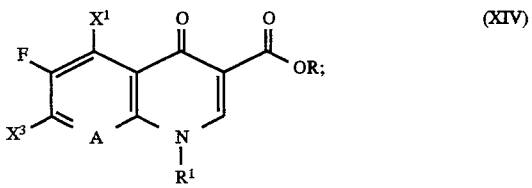

C) reacting the solution of the compound of the formula (XIV) with a heterocyclic compound of the formula

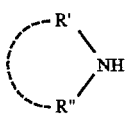

thereby to form a solution of an ester of the formula

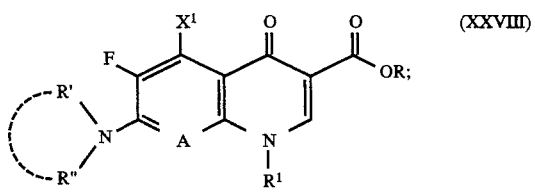

D) hydrolyzing with an alkali to replace R by H; and

E) recovering the compound of the formula (Ia).

2. The process according to claim 1, in which

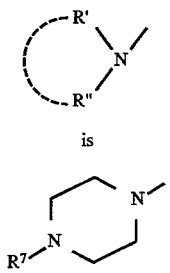

is in which $R^7$ is hydrogen or optionally substituted alkyl or phenyl.

3. The process according to claim 1, in which

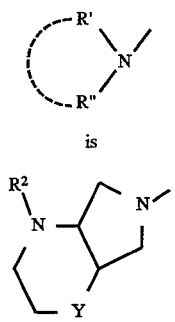

Y is $CH_2$ or O, $R^2$ is H, 5-methyl-2-oxo-1,3-dioxolen-4-yl-methyl, $C_2$-$C_5$-oxoalkyl, $CH_2$—CO—$C_6H_5$, $CH_2CH_2CO_2R_6$, $R_6O_2C$—CH=C—$COR^6$, —CH=CH—$COR^6$ or $CH_2CH_2$—CN, and $R^6$ is hydrogen or $C_1$-$C_3$-alkyl.

4. The process according to claim 3, in which $R^2$ is H, $CH_2$—O—$CH_3$, $CH_2$—O—$C_6H_5$, $CH_2CH_2$—CO—$CH_3$, $CH_2CH_2CO_2R^6$, —CH=$CO_2R^6$ or $CH_2CH_2CN$, and $R^6$ is $C_1$-$C_3$-alkyl.

5. The process according to claim 2, in which

A is CH, $X^1$ represents H, $X^2$ is fluorine or chlorine, $X^3$ is fluorine, and $R^7$ is H or ethyl.

6. The process according to claim 4, in which

A is CCl or CF,

R is $CH_3$ or $C_2H_5$, $R^1$ is cyclopropyl, $X^1$ is H, $X^2$ is fluorine or chlorine, $X^3$ is fluorine, $R^2$ is H, and Y is $CH_2$.

7. The process according to claim 2, wherein the compound of the formula (XVII) is enantiomerically pure.

8. The process according to claim 2, wherein the compound of the formula (XVII) is an enantiomerically pure compound selected from the group consisting of compounds of the formulae (XXIXa) to (XXIXd)

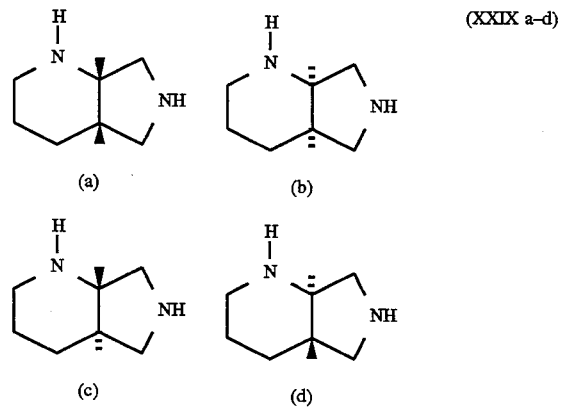

(XXIX a–d)

9. The process according to claim 1, wherein the auxiliary base in step (B) comprises potassium carbonate.

10. The process according to claim 1, wherein the solvent in step (A) is selected from the group consisting of NMP, diglyme, DMEU and tetramethylurea.

11. The process according to claim 1, wherein the solvent in step (A) is NMP.

* * * * *

UNITED STATES PATENT AND TRADEMARK OFFICE
CERTIFICATE OF CORRECTION

PATENT NO. : 5,639,886
DATED : June 17, 1997
INVENTOR(S) : Zerbes, et al.

It is certified that error appears in the above-indentified patent and that said Letters Patent is hereby corrected as shown below:

Col. 19, lines 35-36   Delete " $CH_2CH_2CO_2R_6$ , $R_6O_2C-CH=C-COR^6$ , $-CH=CH-COR^6$ " and substitute -- $CH_2CH_2CO_2R^6$ , $R^6O_2C-CH=C-CO_2R^6$ , $-CH=CH-CO_2R^6$ --

Signed and Sealed this

Twenty-sixth Day of May, 1998

Attest:

BRUCE LEHMAN

Attesting Officer

Commissioner of Patents and Trademarks